United States Patent
Garcia De Leon et al.

(10) Patent No.: US 10,017,831 B2
(45) Date of Patent: Jul. 10, 2018

(54) **BACTERIAL CULTURES OF *ACIDITHIOBACILLUS THIOOXIDANS* AND THEIR USE IN THE TREATMENT OF MATERIALS CONTAINING SULFUR-COMPOUNDS**

(71) Applicants: INSTITUTO MEXICANO DEL PETROLEO, Mexico City (MX); INSTITUTO POLITECNICO NACIONAL, Mexico City (MX)

(72) Inventors: Roberto Garcia De Leon, Mexico City (MX); Norma Gabriela Rojas Avelizapa, Mexico City (MX); Jorge Arturo Aburto Anell, Mexico City (MX); Regina Hernandez Gama, Mexico City (MX); Marlenne Gomez Ramirez, Mexico City (MX)

(73) Assignees: INSTITUTO MEXICANO DEL PETROLEO, Mexico City (MX); INSTITUTO POLITECNICO NACIONAL, Mexico City (MX)

( * ) Notice: Subject to any disclaimer, the term of this patent is extended or adjusted under 35 U.S.C. 154(b) by 0 days.

(21) Appl. No.: 14/738,032

(22) Filed: Jun. 12, 2015

(65) Prior Publication Data
US 2015/0361513 A1 Dec. 17, 2015

(30) Foreign Application Priority Data
Jun. 13, 2014 (MX) .................... MX/a/2014/007119

(51) Int. Cl.
| | | |
|---|---|---|
| *C12N 1/20* | (2006.01) | |
| *C12R 1/01* | (2006.01) | |
| *C12Q 1/04* | (2006.01) | |
| *C12P 3/00* | (2006.01) | |

(52) U.S. Cl.
CPC .................. *C12R 1/01* (2013.01); *C12N 1/20* (2013.01); *C12P 3/00* (2013.01); *C12Q 1/04* (2013.01)

(58) Field of Classification Search
None
See application file for complete search history.

(56) References Cited

U.S. PATENT DOCUMENTS 6,063,158 A * 5/2000 Sharp .................. C22B 3/18
423/DIG. 17

OTHER PUBLICATIONS

Giaveno et al., Use of bioreactors in the leaching of an oxidized copper ore. Lat. Am. Appl. Res. [online]. 2003, vol. 33, n. 1 [cited Oct. 31, 2016], pp. 13-18 . Available at: <http://www.scielo.org.ar/scielo.php?script=sci_arttext&pid=S0327-07932003000100003&lng=es&nrm=iso>.*
Johansson et al., (presented in 1999 in Madrid), (http://technology.infomine.com/biometmine/biopapers/Copper_from_Chalcopyrite.pdf).*

* cited by examiner

*Primary Examiner* — Irene Marx
(74) *Attorney, Agent, or Firm* — Dickinson Wright PLLC

(57) ABSTRACT

Bacterial cultures of *Acidithiobacillus thiooxidans* are isolated, maintained and identified and used in the treatment of materials containing sulfur-compounds, such as contaminated and/or spent catalysts with elemental sulfur (S). Bacterial cultures of *Acidithiobacillus thiooxidans* exhibit sulfur-oxidizing activity particularly useful in the transformation of elemental sulfur (S) to sulfates ($SO_4$), a compound soluble in water ($H_2O$) and usable in industry. The bacterial cultures of *Acidithiobacillus thiooxidans* are mainly used as a biological or biotechnological procedure for the treatment of contaminated and/or spent catalysts with elemental sulfur (S) hazardous contaminated wastes that are mainly, but not exclusively, from the Claus process that operates at environmental conditions; does not impact the environment or ecosystem; and recovers 91-100% of the elemental sulfur (S) in sulfate form ($SO_4$).

11 Claims, 6 Drawing Sheets

BACTERIAL CULTURES OF
*ACIDITHIOBACILLUS THIOOXIDANS* AND
THEIR USE IN THE TREATMENT OF
MATERIALS CONTAINING
SULFUR-COMPOUNDS

CROSS-REFERENCE TO RELATED
APPLICATION

This application claims the benefit and priority under 35 U.S.C. § 119 to Mexican Patent Application No. MX/a/2014/007119 with a filing date of Jun. 13, 2014, the disclosure of which is incorporated herein by reference in its entirety.

FIELD OF THE INVENTION

The present invention relates to bacterial cultures of *Acidithiobacillus thiooxidans*, their isolation method, maintenance and identification, and their use in the treatment of materials containing sulfur-compounds, such as contaminated and/or spent catalysts with sulfur (S), among others.

Bacterial cultures of *Acidithiobacillus thiooxidans*, of the present invention, exhibit a sulfur-oxidizing activity particularly useful in the transformation of elemental sulfur (S) to sulfates ($SO_4$), a compound which is soluble in water ($H_2O$), being usable in the general industry.

BACKGROUND OF THE INVENTION

The activities of the oil industry have created serious environmental problems resulting from the intrinsic operations of the processes of exploration, production, refining, distribution and use of hydrocarbons. Hydrogen sulfide ($H_2S$) is a smelly, corrosive, highly toxic gas, which is generated as part of the oil industry activities. Hydrogen sulfide is commonly found in the form of natural gas and is particularly obtained if the oil contains high concentration of sulfur compounds, such as oil in Mexico. Since $H_2S$ is a pollutant substance, it seeks to be transformed into elemental sulfur, which has a greater use in the general industry.

Nowadays, the process used for the recovery of $H_2S$ in oil activities is known as Claus Process, which has become a standard in the oil industry. Its inventor, the scientist Carl Friedrich Claus patented the Claus process in 1883.

The Claus process involves separating the $H_2S$ from the gas stream using an extraction with liquid solutions of various alkyl amines, commonly referred as amines. There are different types of amines which are used in the Claus process, such as monoethanolamine (MEA), diethanolamine (DEA), methyldiethanolamine (MDEA), diisopropylamine (DIPA), and the ethoxy ethanol amine also known as diglycolamine (DGA); being the MEA, DEA and MDEA, the alkyl amines more used.

In the Claus process, $H_2S$ is fed to a Claus unit, resulting in two stages:
 a) A thermal stage, where $H_2S$ is partially oxidized with air, this occurs in a reaction oven at high temperatures from 1000 to 1400° C., forming elemental sulfur (S) and sulfur dioxide ($SO_2$), but remains $H_2S$ unreacted; and
 b) A catalytic stage, where the remaining $H_2S$ reacts with $SO_2$ at low temperatures, around 200-350° C., over a catalyst to form and depleted in elemental sulfur (S).

The Claus process uses different types of industrial catalysts, such as titanium oxide catalyst, alumina, zeolites, clays, silico-aluminates, porous, among others.

The $H_2S$ deactivates industrial catalysts, such as catalysts of titanium oxide, ($TiO_2$) and others mentioned above. Once exhausted by elemental sulfur (S) and/or deactivated, the catalysts used in the Claus process become polluting and hazardous wastes.

Currently, exhausted and/or deactivated industrial catalysts in the Claus process are disposed in sites established by environmental legislation for the disposal of hazardous wastes, seeking to minimize damages to the environment and ecosystem, but with an environmental impact because they are still hazardous wastes. Moreover, the recovery of elemental sulfur (S) is still missing, which has a greater use in the general industry. Based on the technique state of art, the treatment of catalysts contaminated and/or spent has been basically focused to the recovery of catalysts which contain or may contain different metals such as copper (Cu), iron (Fe), aluminum (Al), nickel (Ni), cobalt (Co), vanadium (V) and molybdenum (Mo).

Regarding catalysts contaminated and/or spent with sulfur, there is no treatment.

The Mexican patent MX 167.308 (B), Mar. 15, 1993 relates to a process for regenerating a catalyst contaminated with sulfur, comprising a zeolite and a Group VIII metal which process is characterized because involves agglomerating the Group VIII metal and subsequently separating the sulfur from the catalyst, with a focus on the chemical treatment of separation of the aforementioned metals.

None of the mentioned references suggest or even less claim bacterial cultures of *Acidithiobacillus thiooxidans*, their isolation method, maintenance and identification, and their use in the treatment of materials containing sulfur-compounds, such as contaminated and/or spent catalysts with elemental sulfur (S).

SUMMARY OF THE INVENTION

The present invention provides bacterial cultures of *Acidithiobacillus thiooxidans*, specifically the bacterial strains:
 *Acidithiobacillus thiooxidans* AZCT-M125-5, registration number DSM 26636, and
 *Acidithiobacillus thiooxidans* AZCT-M125-6, registration number DSM 26637,
registered on Nov. 12, 2012 to the international authority of the Deposit of Microorganisms Leibniz Institute DSMZ-German Collection of Microorganisms and Cell Cultures, for the purposes of patent procedure, in accordance with the Budapest Agreement. The cultures were deposited at Leibniz-Institut DSMZ-Deutsche Sammlung von Mikroorganismen and Zellkulturen GmbH, Leibniz Institute DSMZ-German Collection of Microorganisms and Cell Cultures, Inhoffenstraße 7B, 38124 Braunschweig, GERMANY. Taxonomic description: Analysis based on 16S rRNA gene sequences indicated that microbial cultures AZCT-M125-5 and AZCT-M125-6 were closely related to *Acidithiobacillus thiooxidans* of the gamma subclass of Proteobacteria, Gram-negative, rod-shape bacterium, chemolithoautotrophic that uses sulfur as energy source and carbon dioxide as carbon source. It is mesophilic and isolated from soil, and is able to grow using elemental sulfur at concentrations higher than 1% and up to 9% (w/v) and is able to produce sulfates within pH 3 to 7.

According to one embodiment of the present invention, a method is provided for isolation of bacterial cultures of *Acidithiobacillus thiooxidans*, maintenance and identification of bacterial strains *Acidithiobacillus thiooxidans* AZCT-M125-5 and AZCT-M125-6, with registration numbers DSM 26636 and DSM 26637 respectively, which have sulfur-oxidizing activity, particularly useful in the transformation of elemental sulfur (S) to sulfates ($SO_4$), a compound which is soluble in water ($H_2O$), being usable in the general industry.

The method comprises a) Isolation of the bacterial cultures from their natural environment in a liquid culture media that involves a sulfur source;

b) Maintenance in a modified Starkey medium, added with 5 to 15 g/l of elemental sulfur [S], at pH from 2 to 4, preferably 10 g/l of elemental sulfur [S], to a pH from 2.5-3; and c) Molecular identification preferably by a phylogenetic tree build using the method known as Unweighted Pair Group Method Arithmetic mean (UPGMA).

Another embodiment of the present invention provides, as a main use of the bacterial cultures of *Acidithiobacillus thiooxidans*, preferably bacterial strains *Acidithiobacillus thiooxidans* AZCT-M125-5 and AZCT-M125-6 with registration numbers DSM 26636 and DSM 26637 respectively, a biological or biotechnological process for the treatment of contaminated and/or spent catalysts with elemental sulfur (S), hazardous waste pollutants that came mainly, but not exclusive, from the Claus process, that:

Works at environmental conditions;
Does not impact to the environment or ecosystem; and
Recovers 91-100% of elemental sulfur (S) in the form of sulfates ($SO_4$), a compound that is soluble in water ($H_2O$), for future reuse or for a safe disposal of catalysts.

Figure 1:
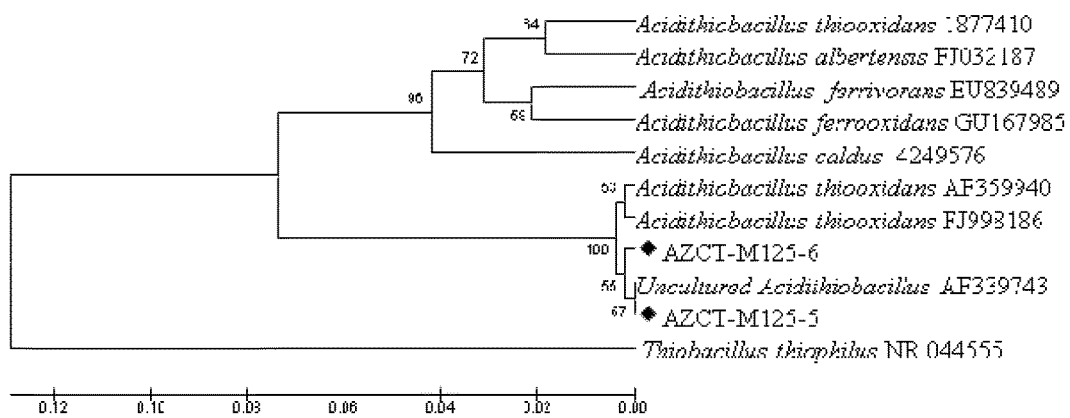
FIG. 1 shows a phylogenetic tree of 16S rRNA gene sequences of bacterial strains identified as *Acidithiobacillus thiooxidans* AZCT-M125-5 and AZCT-M125-6, with registration numbers DSM 26636 and DSM 26637 respectively.

*Acidithiobacillus thiooxidans* AZCT-M125-5, registration number DSM 26636, and

*Acidithiobacillus thiooxidans* AZCT-M125-6, registration number DSM 26637.

DETAILED DESCRIPTION OF THE INVENTION

The present invention relates to bacterial cultures of *Acidithiobacillus thiooxidans*, their isolation method, maintenance and identification, and their use in the treatment of materials containing sulfur-compounds, such as contaminated and/or spent catalysts with elemental sulfur (S).

Bacterial cultures of *Acidithiobacillus thiooxidans* that preferably employ the present invention are bacterial strains:

*Acidithiobacillus thiooxidans* AZCT-M125-5, registration number DSM 26636, and

*Acidithiobacillus thiooxidans* AZCT-M125-6, registration number DSM 26637, registered on Nov. 12, 2012 to the international authority of biological material deposit Leibniz-Institute DSMZ-German Collection of Microorganisms and Cell Cultures, for the purposes of patent procedure, in accordance with the Budapest Agreement.

The actual invention also relates to a method for bacterial culture isolation of *Acidithiobacillus thiooxidans*, maintenance and identification of bacterial strains *Acidithiobacillus thiooxidans* AZCT-M125-5 and AZCT-M125-6, with registration numbers DSM 26636 and DSM 26637 respectively which exhibit a particularly useful sulfur-oxidizing activity transforming elemental sulfur (S) to sulfates ($SO_4$), a compound which is soluble in water ($H_2O$), being usable in the general industry.

The present invention further relates to a biological or biotechnological method employing bacterial cultures of *Acidithiobacillus thiooxidans*, preferably bacterial strains *Acidithiobacillus thiooxidans* AZCT-M125-5 and AZCT-M125-6, with registration numbers DSM 26636 and DSM 26637 respectively, for the treatment of contaminated and/or spent catalysts with elemental sulfur (S), hazardous waste pollutants mainly, but not exclusive, from Claus Process, that:

Works at environmental conditions;
Does not impact the environment or ecosystem; and
Recovers 91-100% elemental sulfur (S) in the form of sulfates ($SO_4$), a compound that is soluble in water ($H_2O$), for future reuse or safe disposal of the catalysts.

At the end of the biotechnological treatment the industrial catalysts treated can be disposed in a safer form, that is, do not represent an exposition risk to human.

Contaminated and/or spent catalysts with elemental sulfur (S), that came mainly, but not exclusive, from the Claus process, are used either in the form of pellets or powder:

The powder form of the catalyst is obtained as a result of grinding the same catalyst, and
The pellet form of the catalyst is as found in the Claus process.

The compound content of elemental sulfur (S) in the catalyst contaminated and/or spent is variable, from 0.1 to 9% w/v.

The development of the present invention comprised the following stages:

Isolation Method of *Acidithiobacillus thiooxidans* Bacterial Cultures, Maintenance and Identification of Bacterial Strains *Acidithiobacillus thiooxidans* AZCT-M125-5 and AZCT-M125-6, with Registration Numbers DSM 26636 and DSM 26637 Respectively.

I. Isolation of a bacterial cultures sample of *Acidithiobacillus thiooxidans* from their natural environment, preferably from the Natural Park Los Azufres, in Ciudad Hidalgo in Michoacan de Ocampo State, Mexico, in a liquid culture medium comprising a sulfur source, preferably in a liquid culture medium called ATCC 125 (American Type Culture Collection) based on mineral salts whose composition is shown in Table No. 1, added with 0 to 15 g/L of elemental sulfur [S], at pH 2 to 10, preferably 5 to 10 g/l of elemental sulfur [S], and a pH of 3.

TABLE 1

Composition of ATCC 125 liquid medium, used for isolation of bacterial cultures of *Acidithiobacillus thiooxidans*, added with 0 to 15 g/L of elemental sulfur [S], at pH of 2 to 10, preferably 5 to 10 g/L of elemental sulfur [S], at pH of 3.

| Composition | Interval g/L | Preferential g/L |
|---|---|---|
| $KH_2PO_4$ | 2-4 | 3.0 |
| $(NH_4)_2SO_4$ | 0.1-0.3 | 0.2 |
| $MgSO_4 7H_2O$ | 0.2-0.8 | 0.5 |
| $CaCl_2 \cdot 2H_2O$ | 0.1-0.5 | 0.3 |
| $FeSO_4 \cdot 7H_2O$ | 0.00-0.02 | 0.01 |

II. Preparation of a maintenance medium for bacterial cultures of *Acidithiobacillus thiooxidans*, known as modified Starkey medium, which is shown in Table No. 2, added with 5 to 15 g/l of elemental sulfur [S], at a pH of 2 to 4, preferably 10 g/l elemental sulfur [S], at pH of 2.5-3.

TABLE 2

Composition of modified Starkey culture medium, used for maintenance of bacterial cultures of *Acidithiobacillus thiooxidans*, added with 5 to 15 g/l of elemental sulfur [S], at pH of 2 to 4, preferably 10 g/l of elemental sulfur [S], at pH of 2.5-3.

| Composition | Interval g/L | Preferential g/L |
|---|---|---|
| $KH_2PO_4$ | 2-4 | 3.0 |
| $(NH_4)_2SO_4$ | 0.1-0.3 | 0.2 |
| $MgSO_4 7H_2O$ | 0.2-0.8 | 0.5 |
| $CaCl_2 \cdot 2H_2O$ | 0.1-0.5 | 0.3 |
| $FeSO_4 \cdot 7H_2O$ | 0.00-0.02 | 0.01 |
| $Na_2MoO_4$ | 50-100 µg | 75 µg |

III. Molecular identification of bacterial cultures of *Acidithiobacillus thiooxidans*. FIG. 1 shows identification of the bacterial cultures of *Acidithiobacillus thiooxidans*, specifically of the bacterial strains:
*Acidithiobacillus thiooxidans* AZCT-M125-5, registration number DSM 26636, and
*Acidithiobacillus thiooxidans* AZCT-M125-6, registration number DSM 26637,
by means of a phylogenetic tree constructed using the method known as Unweighted Pair Group Method Arithmetic mean (UPGMA). Sequencing of the 16S rRNA gene of the bacterial cultures of *Acidithiobacillus thiooxidans* are available with GenBank accession number: JX134585 and JX134586. GenBank is used for the collection of equivalent genes in other organisms to further comparison. This routine procedure in molecular biology is well known, so the bacterial cultures were identified as *Acidithiobacillus thiooxidans*.

In this regard, it is important to emphasize bacterial strains:
*Acidithiobacillus thiooxidans* AZCT-M125-5, registration number DSM 26636, and
*Acidithiobacillus thiooxidans* AZCT-M125-6, registration number DSM 26637, preferably employed by the present invention were registered on Nov. 12, 2012 to the international authority of microorganisms deposit Leibniz-Institute DSMZ-German Collection of Microorganisms and Cell Cultures, for the purposes of the patent procedure, in accordance with the Budapest Agreement.

Evaluation of Bacterial Cultures of *Acidithiobacillus thiooxidans*, Specifically the Bacterial Strains *Acidithiobacillus thiooxidans* AZCT-M125-5 and AZCT-M125-6, with Registration Number DSM 26636 and DSM 26637 Respectively, for the Transformation of Elemental Sulfur-Ccompounds (S) to Sulfates ($SO_4$).

IV. The evaluation of bacterial cultures of *Acidithiobacillus thiooxidans* is done by using different concentrations of catalyst contaminated and/or spent, as for example the catalysts of titanium oxide, alumina, zeolite, clays, silicoaluminates, porous, among others.

Figure 2:
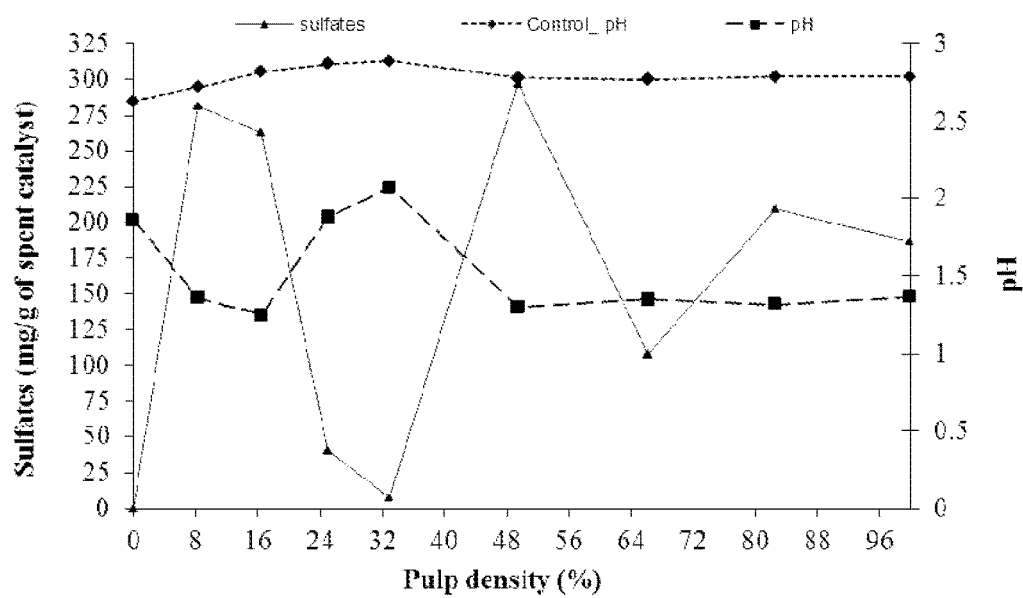
FIG. 2 shows the results of the evaluation assays of the bacterial strain *Acidithiobacillus thiooxidans* AZCT-M125-5, with registration number DSM 26636, in a modified Starkey medium, at different concentrations of a spent industrial catalyst with elemental sulfur (S)
Figure 3:
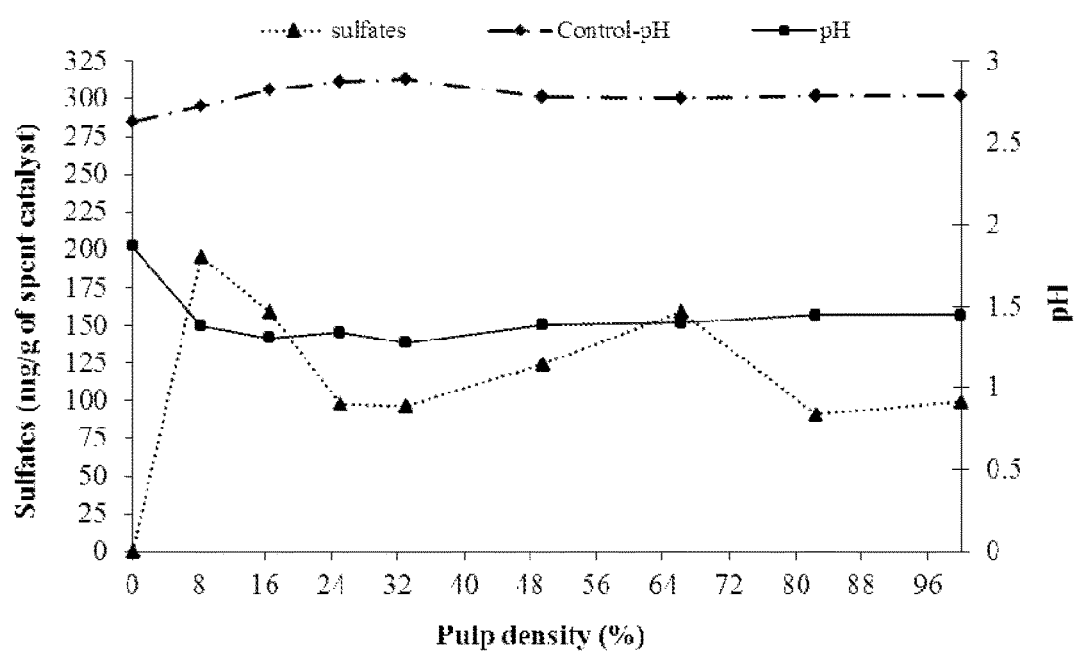
FIG. 3 shows the results of the evaluation assays of the bacterial strain *Acidithiobacillus thiooxidans* AZCT-M125-6, with registration number DSM 26637, in a modified Starkey medium, at different concentrations of a spent industrial catalyst with elemental sulfur (S)

FIGS. 2 and 3 show the results of evaluation assays of the bacterial strains *Acidithiobacillus thiooxidans* AZCT-M125-5 and AZCT-M125-6, with registration numbers DSM 26636 and 26637, respectively, at different concentrations of the spent catalyst of titanium oxide ($TiO_2$) from 8 to 100 g per weight/100 ml (8 to 100% weight/volume), containing at the same time different concentrations of elemental sulfur (S) from 0.7 to 8.6% weight/volume, in a liquid medium (modified Starkey) at a temperature of 25 a 35° C., at 140 rpm during 7 days.

In such figures, the effect of the concentration of titanium oxide catalyst contaminated with elemental sulfur (S) on the sulfur-oxidizing activity of the bacterial cultures of *Acidithiobacillus thiooxidans* and the pH decreasing due to the sulfuric acid production ($H_2SO_4$) by the bacterial cultures of *Acidithiobacillus thiooxidans* is observed.

According to the obtained results, the decision was to work with the bacterial strains *Acidithiobacillus thiooxidans* AZCT-M125-5 and AZCT-M125-6, with registration numbers DSM 26636 and 26637, respectively, since present the capacity to transform elemental sulfur-compounds (S) to sulfates ($SO_4$) for performing the biotechnological treatment of the spent catalyst with elemental sulfur (S) in a glass column system.

Preparation of Active Inocula.

V. The preparation of active inocula consists on growing each of the bacterial cultures of *Acidithiobacillus thiooxidans*, specifically the bacterial strains *Acidithiobacillus thiooxidans* AZCT-M125-5 and AZCT-M125-6, with registration numbers DSM 26636 and DSM 26637 respectively, in 125 Erlenmeyer flasks, containing 30 ml of modified Starkey media added with elemental sulfur at 1% weight/volume and adjusted to pH 3, afterwards flasks were incubated at 30° C., 140 rpm during 4 days.

Preparation of Inoculation Media.

VI. The preparation of inoculation media consists of taking 2 ml from the active inocula, then depositing it in approximately 8 ml of the modified Starkey media (without sulfur), and adjusted to pH 3.

Use of Inoculation Media in a Glass Column System.

VII. The use of inoculation media in a glass column system consists into pack 8-glass column system, per each of the bacterial strains, with the catalyst contaminated and/or spent with 8 g of elemental sulfur (S), where 5-glass columns were inoculated, 3-glass columns were coded as controls, and they were not inoculated.

The 5 columns coded as inoculated were added with a known volume of 10 ml of modified Starkey media (without sulfur), which contain the active inocula of the bacterial strains *Acidithiobacillus thiooxidans* AZCT-M125-5 or AZCT-M125-6, with registration numbers DSM 26636 and 26637 respectively, at a concentration of $2\times10^6$ colony forming units per milliliter (CFU/ml).

The 3-glass columns that were not inoculated were also added with a known volume of 10 ml of modified Starkey media (without sulfur).

Once done previous, air was supplied in a vertical form with a descendent flow of 80 ml/min by means of a hose assembly of air delivery. The glass column can be of 30 cm long×1.5 cm wide and has a descendent aeration output in the central part of the column and in the inferior part with a petcock. In the bottom part of the glass column it is located a bed of glass fiber that function as support for the contaminated catalyst.

The treatment was aerated using a hose assembly for air delivery that was located at the central part of each of the glass columns, having an airflow of 80 ml/min.

The treatment was done during 28 days with the culture that contained the bacterial strain *Acidithiobacillus thiooxidans* AZCT-M125-5 with registration number DSM 26636 and 35 days with the culture that contained the bacterial strain *Acidithiobacillus thiooxidans* AZCT-M125-6 with registration number DSM 26637, been the glass columns aerated in a continuous form.

Due to water loss during the treatment, modified Starkey media (without sulfur) was added using a pipet in the top of the glass column, maintaining a ratio weight/volume of 8:10 at a preference temperature of 30° C. The total amount of modified Starkey media without sulfur added corresponded to 1.2 ml per day.

Monitoring of the Treatment of the Material Contaminated and/or Spent with Sulfur.

VIII. The monitoring or sampling of the biotechnological treatment of the spent catalyst with sulfur consists into take out a sample each 7 days of the glass column system from the treatment and other from the called controls to evaluate the effectivity of the treatment. Such monitoring of the treatment consists in a liquid sample, which is subjected to analyses of pH, cell count, sulfur-oxidizing activity that is sulfates ($SO_4$) concentration. In the treated catalyst it was determined the residual concentration of elemental sulfur (S) by means of inductively coupled plasma optical emission spectrometry.

Figure 4:
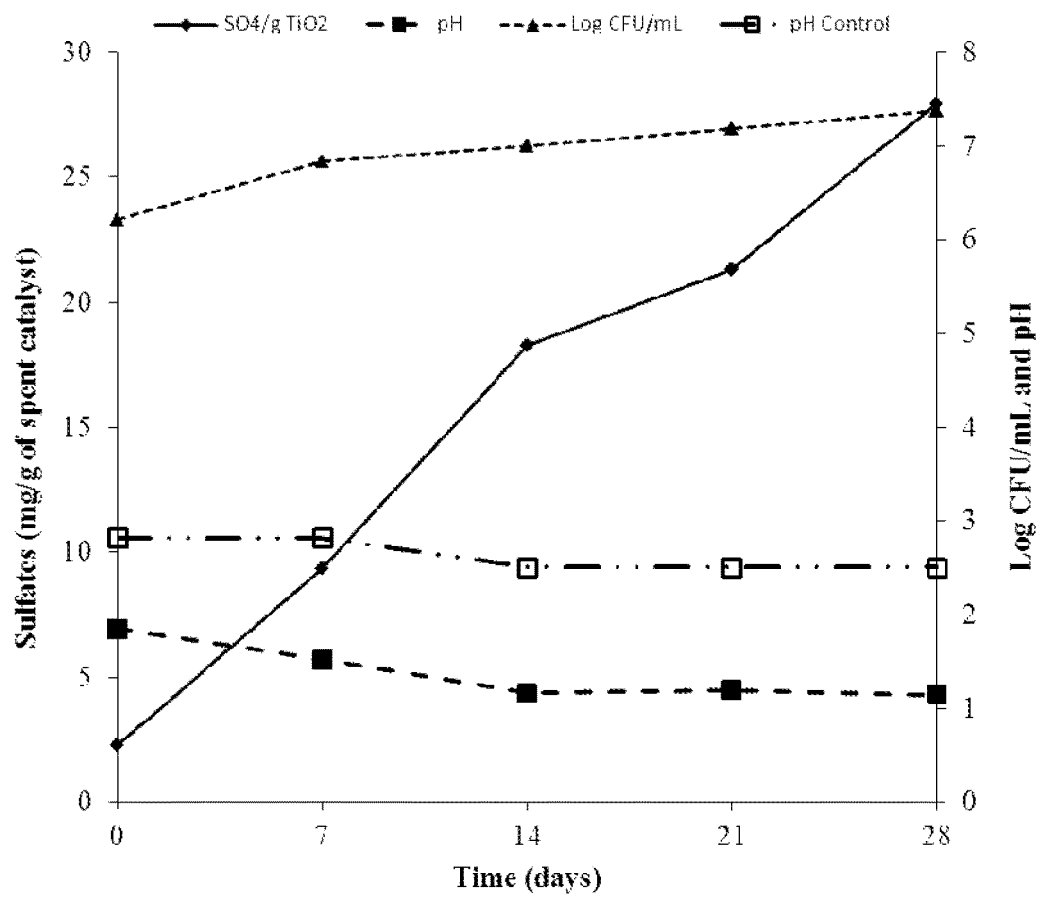
FIG. 4 shows the monitoring of the biotechnological treatment of spent industrial catalyst with elemental sulfur (S) considering the parameters of microbial growth by counting cells in a Neubauer chamber, pH and sulfates produced by bacterial strain *Acidithiobacillus thiooxidans* AZCT-M125-5, with registration number DSM 26636.
Figure 5:
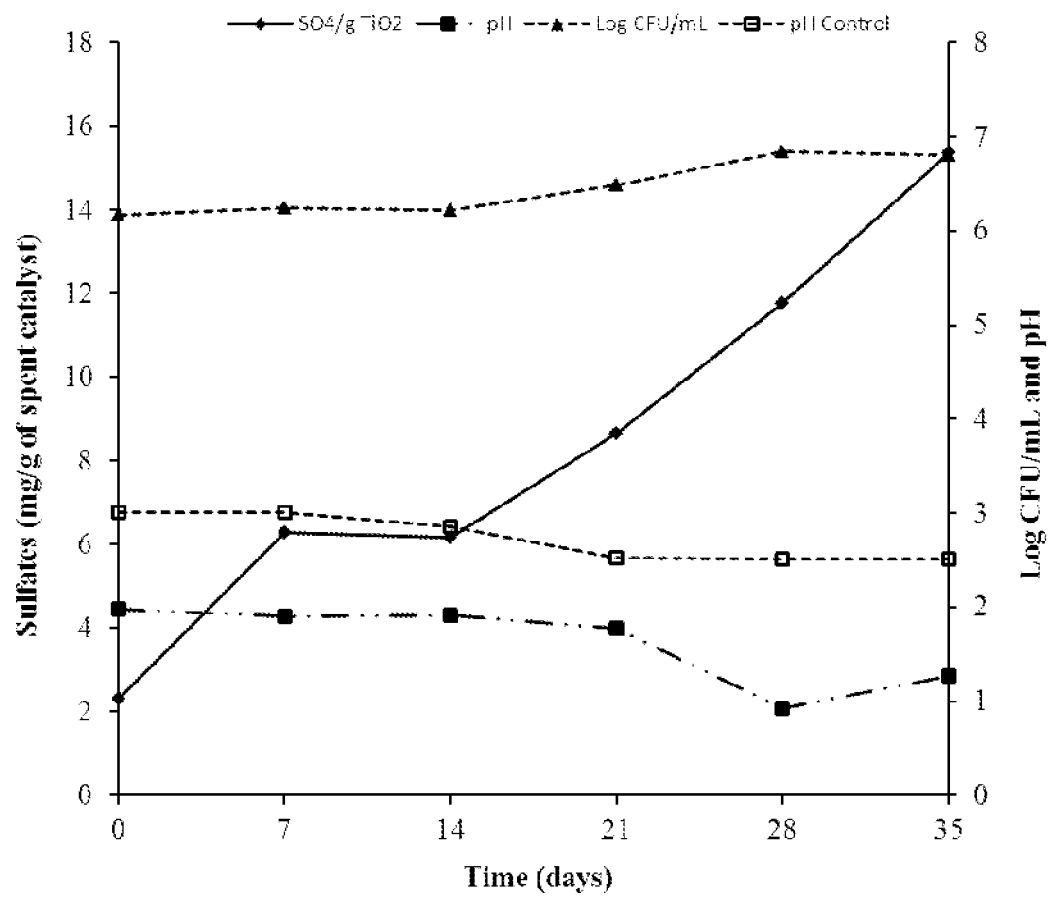
FIG. 5 shows the monitoring of the biotechnological treatment of spent industrial catalyst with elemental sulfur (S) considering the parameters of microbial growth by counting cells in a Neubauer chamber, pH and sulfates produced by bacterial strain *Acidithiobacillus thiooxidans* AZCT-M125-6, with registration number DSM 26637.

FIGS. 4 and 5 show the monitoring of the treatment of the spent catalyst with sulfur considering the parameters of growth evaluated by cell count in a Neubauer chamber (CFU/ml), which indicated that:

The bacterial culture of *Acidithiobacillus thiooxidans* AZCT-M125-5 with registration number DSM 26636 present an increment in population density from $1.62\times 10^6$ CFU/ml al time cero to values of $2.38\times10^7$ CFU/ml at the end of treatment that is 28 days.

The bacterial culture of *Acidithiobacillus thiooxidans* AZCT-M125-6 with registration number DSM 26637 present an increment in population density from $1.74\times 10^6$ CFU/ml at time cero to values of $6.32\times10^6$ CFU/ml at the end of treatment, that is, 35 days.

Previous data is indicative that bacterial cultures of *Acidithiobacillus thiooxidans* are using the elemental sulfur (S) as an energy source for their chemiolitothrophic growth.

FIGS. 4 and 5 also show the monitoring of the treatment of the spent catalyst with sulfur respect to the parameter of pH, where it is observed that:

The treatment with the bacterial culture of *Acidithiobacillus thiooxidans* AZCT-M125-5 with registration number DSM 26636 causes a pH decrease from pH 1.85 to pH 1.15 after 28 days of treatment.

The bacterial treatment with the bacterial culture of *Acidithiobacillus thiooxidans* AZCT-M125-6 with registration number DSM 26637 causes a pH decrease from pH 1.95 to pH 1.27 after 35 days of treatment.

The above is an indirect indicative of the sulfuric acid production ($H_2SO_4$) and/or sulfates ($SO_4$), due to the sulfur-oxidizing activity of the evaluated bacterial cultures of *Acidithiobacillus thiooxidans*. In the columns called controls did not observe a pH significant variation.

FIGS. 4 and 5 show the monitoring of the treatment of the catalyst contaminated with sulfur respect to sulfates production ($SO_4$). Results of the treatment allowed determining that from the first days of incubation it was observed sulfur-oxidizing activity.

For the bacterial culture of *Acidithiobacillus thiooxidans* AZCT-M125-5 with registration number DSM 26636, it was observed an increment in sulfates ($SO_4$) concentration in liquid culture, reaching values of 27.94 mg of sulfates/g of spent catalyst, after 28 days of treatment.

For the bacterial culture of *Acidithiobacillus thiooxidans* AZCT-M125-6 with registration number DSM 26637, it was observed an increment in sulfates ($SO_4$) concentration in liquid media, reaching values of 15.35 mg of sulfates/g of spent catalyst, after 35 days of treatment.

Figure 6:
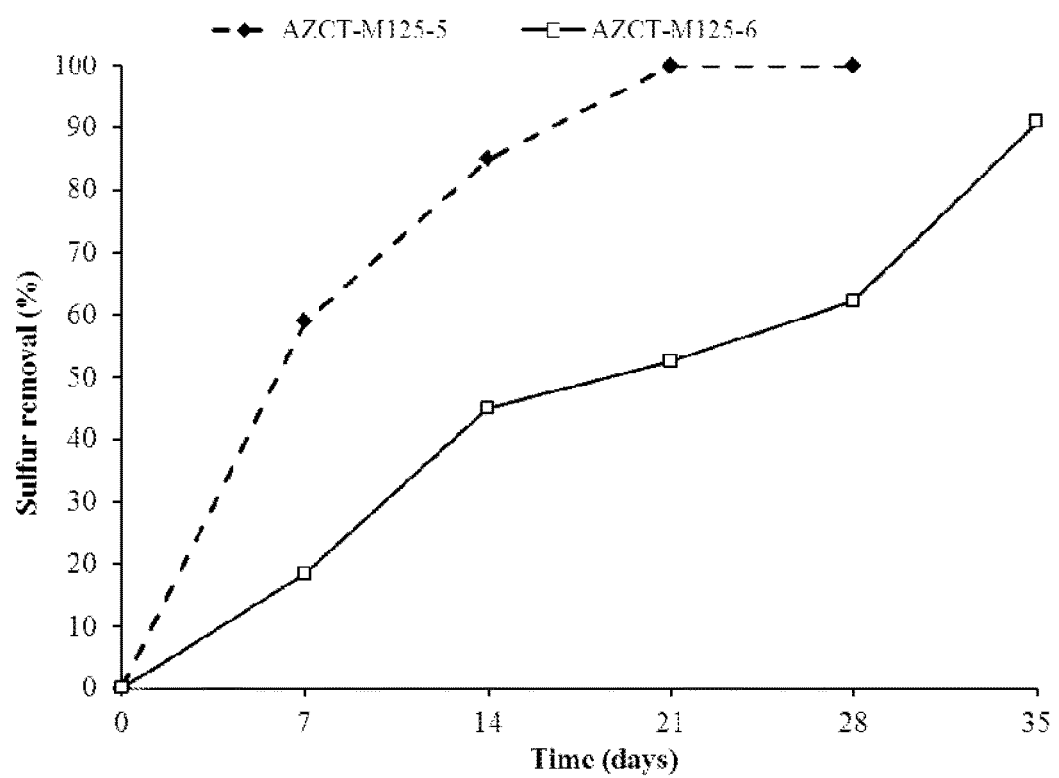
FIG. 6 shows the monitoring of the treatment of industrial spent catalyst with elemental sulfur (S) considering the parameter of elemental sulfur (S) remaining in the spent catalyst as a corresponding percentage of sulfur removed by the bacterial strains.

In FIG. 6, it can be observed that the percentage of total elemental sulfur (S) removed in the spent catalyst increases according time, which demonstrates that there is sulfur-oxidizing activity due to the treatment with both bacterial cultures of *Acidithiobacillus thiooxidans* specifically of the bacterial strains *Acidithiobacillus thiooxidans* AZCT-M125-5 and AZCT-M125-6, with registration number DSM 26636 and DSM 26637 respectively.

Results of the biotechnological procedure for the treatment of spent catalyst with sulfur showed:

A removal of 100% of elemental sulfur (S) contained in the spent catalyst for the bacterial culture *Acidithiobacillus thiooxidans* AZCT-M125-5 with registration number DSM 26636 from 21 days of treatment, that is, from 0.73% of elemental sulfur content reach values same to zero.

For the culture *Acidithiobacillus thiooxidans* AZCT-M125-6 with registration number DSM 26637, the sulfur removal in the spent catalyst correspond to 91% at 35 days of treatment, that is, from 0.73% of elemental sulfur content in the catalyst reach values of 0.066% of residual elemental sulfur in the catalyst.

Therefore, it is shows the efficiency of the use of these bacterial cultures of *Acidithiobacillus thiooxidans* to treat the element sulfur (S) present in a spent catalyst, such as the catalysts of titanium oxide ($TiO_2$) used in the Claus process.

What is claimed is:

1. A biological or biotechnological process for the treatment of spent catalyst containing sulfur-compounds, which involves:
    a) obtaining bacterial cultures of *Acidithiobacillus thiooxidans*;
    b) Preparation of inocula by growing *Acidithiobacillus thiooxidans* DSM 26636 and *Acidithiobacillus thiooxidans* DSM 26637 in Starkey basal media containing $Na_2MoO_4$ adjusted to pH 3 comprising $KH_2PO_4$, $(NH_4)_2SO_4$, $MgSO_47H_2O$, $CaCl_22H_2O$, $FeSO_47H_2O$ and $Na_2MoO_4$, and thereafter incubating at 30° C. while stirring at 140 rpm for 4 days;
    c) Preparation of inoculation media from said inocula of step (b) in said Starkey basal medium containing $Na_2MoO_4$;

d) introducing said inoculation media in a glass column system containing said spent catalyst to be treated; and e) converting elemental sulfur-compounds (S) in said spent catalyst to sulfates ($SO_4$) and removing the sulfur-compounds from said spent catalyst.

2. The biological or biotechnological process for the treatment of spent catalyst containing sulfur-compounds, in accordance with claim 1, where said spent catalyst is obtained from a Claus process.

3. The biological or biotechnological process for the treatment of spent catalyst that contain sulfur-compounds, in accordance with claim 1, where the step b) preparation of inocula, consists of growing the bacterial cultures of *Acidithiobacillus thiooxidans*, in 125 ml Erlenmeyer flasks, containing 30 ml of Starkey media containing elemental sulfur at 1% weight/volume and adjusted to pH 3, and afterwards incubated at 30° C. and 140 rpm for 4 days.

4. The biological or biotechnological process for the treatment of spent catalyst containing sulfur-compounds, in accordance with claim 1, where the step c) Preparation of inoculation media, consists of taking 2 ml from said inocula of step (b) and depositing in approximately 8 ml of said Starkey basal media containing $Na_2MoO_4$ and adjusted to pH 3.

5. The biological or biotechnological process for the treatment of spent catalyst that contain sulfur-compounds, in accordance with claim 4, where the composition of said Starkey basal media containing $Na_2MoO_4$ of step c):

| Composition | Interval g/L |
| --- | --- |
| $KH_2PO_4$ | 2-4 |
| $(NH_4)_2SO_4$ | 0.1-0.3 |
| $MgSO_4 7H_2O$ | 0.2-0.8 |
| $CaCl_2 \cdot 2H_2O$ | 0.1-0.5 |
| $FeSO_4 \cdot 7H_2O$ | 0.00-0.02 |
| $Na_2MoO_4$ | 50-100 µg. |

6. The biological or biotechnological process for the treatment of spent catalyst that contain sulfur-compounds, in accordance with claim 1, where the step d) introducing the inoculation media in a glass column system, consists of packing a glass column system with the spent catalyst that contain sulfur-compounds, where 60% of the columns are inoculated with the inoculation media and 40% of the columns are not inoculated as abiotic systems to determine effectiveness of the biological treatment.

7. The biological or biotechnological process for the treatment of spent catalyst that contain sulfur-compounds, in accordance with claim 1, where the glass column system of the step d), air is supplied in a vertical direction with a descendent flow of 80 ml/min, by means of a hose assembly during 28-35 days maintaining a ratio of 8:10 weight/volume of said spent catalyst to air at a temperature of 30° C.

8. The biological or biotechnological process, for the treatment of spent catalyst that contain sulfur-compounds, in accordance with claim 1, comprising converting 91% to 100% of elemental sulfur (S) to sulfates ($SO_4$) in said spent catalyst.

9. The biological or biotechnological process for the treatment of spent catalyst that contain sulfur-compounds, in accordance with claim 1, comprising determining the concentration of residual elemental sulfur (S) in said spent catalyst by means of inductively coupled plasma optical emission spectrometry.

10. The biological or biotechnological process for the treatment of spent catalyst that contain sulfur-compounds, in accordance with claim 1, wherein the content of residual elemental sulfur in the treated spent catalyst is 0.066%.

11. The process of claim 1, wherein said process treats said spent catalyst and regenerates said spent catalyst by removing sulfur from said spent catalyst, and where said spent catalyst is selected from the group consisting of titanium oxide, alumina, zeolite, clay, and silico-aluminates and contains 0.1 to 9% w/v sulfur as a contaminant.

* * * * *